(12) United States Patent
Everman et al.

(10) Patent No.: US 12,127,853 B2
(45) Date of Patent: Oct. 29, 2024

(54) PHYSIOLOGICAL PARAMETER SENSOR HELMET

(71) Applicant: GMECI, LLC, Beavercreek, OH (US)

(72) Inventors: Brad Everman, Haddonfield, NJ (US); Brian Bradke, Brookfield, VT (US)

( * ) Notice: Subject to any disclaimer, the term of this patent is extended or adjusted under 35 U.S.C. 154(b) by 0 days.

(21) Appl. No.: 17/959,540

(22) Filed: Oct. 4, 2022

(65) Prior Publication Data

US 2024/0115201 A1    Apr. 11, 2024

Related U.S. Application Data

(63) Continuation-in-part of application No. 17/892,542, filed on Aug. 22, 2022, now Pat. No. 12,020,171.

(51) Int. Cl.
   *A61B 5/00* (2006.01)
   *A61B 5/01* (2006.01)
   *A61B 5/1455* (2006.01)

(52) U.S. Cl.
   CPC .............. *A61B 5/6803* (2013.01); *A61B 5/01* (2013.01); *A61B 5/14551* (2013.01); *A61B 5/7264* (2013.01); *A61B 5/746* (2013.01); *A61B 2560/0252* (2013.01); *A61B 2562/0271* (2013.01)

(58) Field of Classification Search
   CPC ..... A61B 5/6803; A61B 5/01; A61B 5/14551; A61B 5/7264; A61B 5/746; A61B 2560/0252; A61B 2562/0271
   See application file for complete search history.

(56) References Cited

U.S. PATENT DOCUMENTS

| | | | |
|---|---|---|---|
| 4,374,301 A * | 2/1983 | Frieder, Jr. ............... | A42B 3/30 379/430 |
| 5,779,631 A * | 7/1998 | Chance ............... | A61B 5/6828 600/328 |
| 8,679,028 B2 | 3/2014 | Melker | |
| 9,298,985 B2 | 3/2016 | Krueger | |
| 10,561,863 B1 | 2/2020 | Dashevsky | |
| 11,426,122 B2 * | 8/2022 | Kamal ................. | A61B 5/6806 |
| 2007/0033029 A1 * | 2/2007 | Sakawaki ........ | G10K 11/17825 704/233 |

(Continued)

FOREIGN PATENT DOCUMENTS

WO    2021/222155 A1    11/2021

*Primary Examiner* — Mark W. Bockelman
(74) *Attorney, Agent, or Firm* — Caldwell Intellectual Property Law

(57) ABSTRACT

Aspects relate to a physiological parameter sensor helmet. The physiological parameter sensor helmet includes at least a helmet including a bone conducting transducer; at least a physiological sensor installed within the at least a helmet, wherein the physiological sensor is configured to measure a plurality of physiological parameters of a user, wherein the plurality of physiological parameters includes at least a plurality of blood oxygenation signals; a computing device in communication with the physiological sensor and including: at least a processor; and a memory communicatively connected to the at least a processor, the memory containing instructions configuring the at least a processor to: receive the plurality of physiological parameters from the physiological sensor; and generate a health profile as a function of the plurality of physiological parameters.

20 Claims, 9 Drawing Sheets

(56) References Cited

U.S. PATENT DOCUMENTS

| | | | | |
|---|---|---|---|---|
| 2014/0123980 A1* | 5/2014 | Rissacher | ............ | A61B 5/6803 128/204.23 |
| 2018/0055134 A1* | 3/2018 | Zhang | .................... | A42B 3/042 |
| 2018/0303392 A1* | 10/2018 | Everman | .............. | A61B 5/6803 |
| 2021/0030097 A1* | 2/2021 | Morgan | ................... | A61B 5/01 |

* cited by examiner

PHYSIOLOGICAL PARAMETER SENSOR HELMET

CROSS-REFERENCE TO RELATED APPLICATIONS

This application is a continuation-in-part of Non-provisional application Ser. No. 17/892,542 filed on Aug. 22, 2022 and entitled "SYSTEMS AND METHODS FOR CORRELATING CUTANEOUS ACTIVITY WITH HUMAN PERFORMANCE," the entirety of which is incorporated herein by reference.

FIELD OF THE INVENTION

The present invention generally relates to the field physiological parameter sensing. In particular, the present invention is directed to a physiological parameter sensor helmet

BACKGROUND

Blood oxygen saturation can determine a plurality of physical characteristics and ailments, including determining whether an individual is on the verge of losing consciousness. Typically, sensors measuring oxygenation are placed on the fingers or foreheads of patients and do not include a means of analyzing the data and alerting the user or a third party of whether an issue has been determined.

SUMMARY OF THE DISCLOSURE

In an aspect a physiological parameter sensor helmet includes at least a helmet including a bone conducting transducer; at least a physiological sensor installed within the at least a helmet, wherein the physiological sensor is configured to measure a plurality of physiological parameters of a user, wherein the plurality of physiological parameters includes at least a plurality of blood oxygenation signals; a computing device in communication with the physiological sensor and including: at least a processor; and a memory communicatively connected to the at least a processor, the memory containing instructions configuring the at least a processor to: receive the plurality of physiological parameters from the physiological sensor; and generate a health profile as a function of the plurality of physiological parameters.

In another aspect a method for generating a health profile of a user, the method including detecting a plurality of physiological parameter utilizing at least a physiological parameter sensor helmet, the physiological parameter sensor helmet including; at least a helmet further including a bone conducting transducer; at least a sensor installed within the at least a helmet, wherein the at least a sensor is configured to measure plurality of physiological parameters of a user's, including at least a plurality of oxygenation signals; generating a health profile utilizing a processor, wherein generating includes: receiving, by a processor, the plurality of physiological parameters from the at least a sensor; and generating, by the processor, the health profile as a function of plurality of physiological parameters.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

In an embodiment, systems, devices and methods disclosed herein detect physiological parameters such as blood oxygen level, blood pressure, neurological oscillations, and heart rate of a user who is operating an item of equipment such as an aircraft through nonintrusive means. Sensors mounted in optimal locations on the head or neck of the user may detect physiological parameters accurately, minimizing interference in activities the user engages in while obtaining a clearer signal than otherwise would be possible. Embodiments of the disclosed device may provide users such as pilots, firemen, and divers who are operating under extreme circumstances with an early warning regarding potential crises such as loss of consciousness, affording the user a few precious extra seconds to avert disaster. Alarms may be provided to the user via bone-conducting transducers or by integration into displays the user is operating, increasing the likelihood that the user will notice the warning in time. Embodiments of devices, systems, and methods herein may enable training for pilots or other persons to function within physiological limitations imposed by their environment, such as hypoxemia imposed by altitude, high G forces and the like; training may further enable users to learn how to avoid total impairment, and to function under partial impairment.

Figure 1:
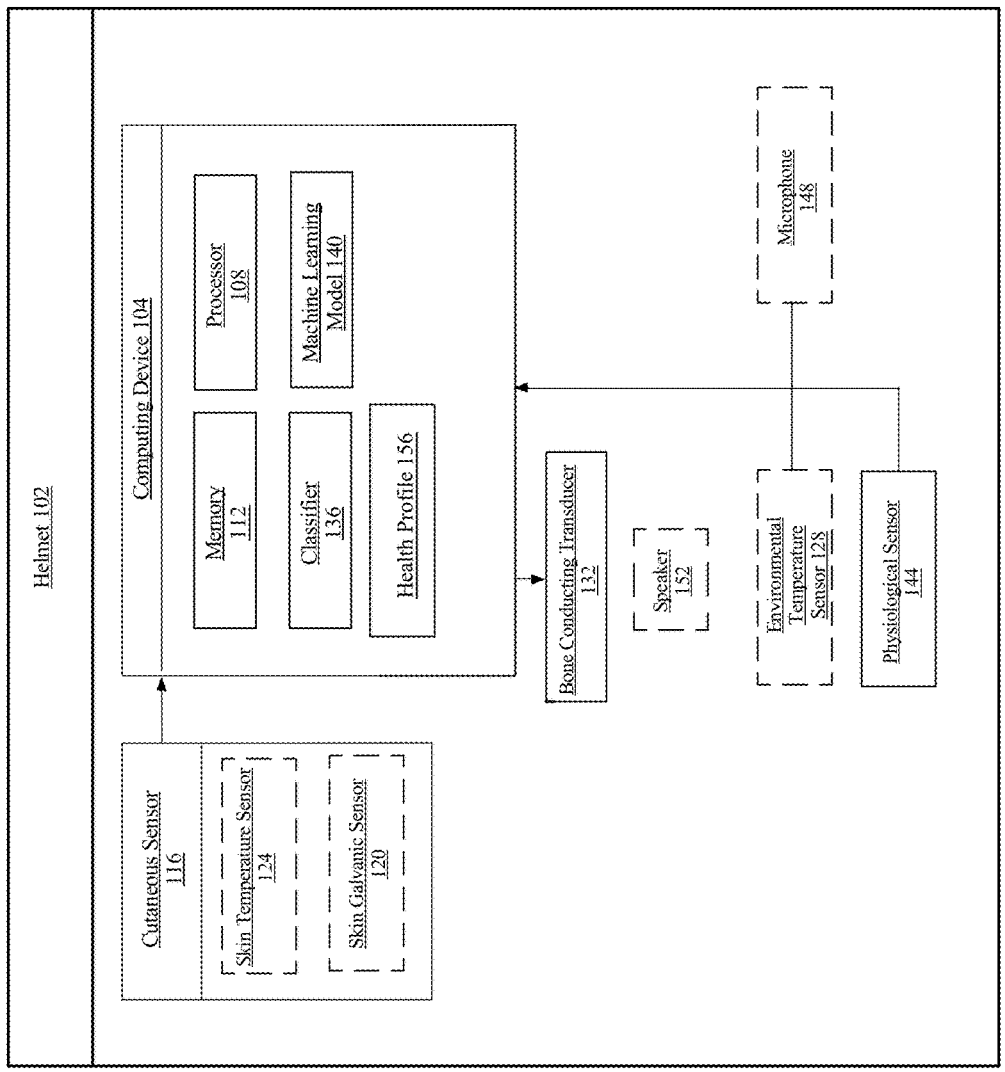
FIG. 1 is a block diagram illustrating an exemplary physiological parameter sensor helmet.

Referring now to FIG. 1, an exemplary embodiment of a physiological parameter sensor helmet 100 is illustrated. Physiological parameter sensor helmet 100 includes a helmet 102. A "helmet," as used in this disclosure, is a headpiece worn by user. Helmet 102, also referred to as "housing" throughout this disclosure, may model helmets used in (or by) aviation (e.g., pilot helmet), first responders (e.g., firefighting helmet), and the like. Physiological parameter sensor helmet 100 may include a computing device 104.

Computing device 104 may include any computing device as described in this disclosure, including without limitation a microcontroller, microprocessor, digital signal processor (DSP) and/or system on a chip (SoC) as described in this disclosure. Computing device 104 may include at least a processor 108. Processor 108 may include any processor described in this disclosure, for example without limitation a microcontroller, microprocessor, digital signal processor (DSP) and/or system on a chip (SoC). Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. processor 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device may include at least a memory 112. Memory 112 may include any memory described in this disclosure, for example without limitation a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. Computing device 104 may be implemented using a "shared nothing" architecture in which data is cached at the worker, in an embodiment, this may enable scalability of physiological parameter sensor helmet 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, physiological parameter sensor helmet 100 may include at least a cutaneous sensor 116. As used in this disclosure, a "cutaneous sensor" is a device that is configured to detect a cutaneous parameter as a function of a cutaneous phenomenon. Cutaneous sensor 116 may be configured to detect at least a cutaneous parameter as a function of a cutaneous phenomenon. As used in this disclosure, a "cutaneous parameter" is a representation of a cutaneous phenomenon. Exemplary cutaneous parameters include, without limitation, measures skin temperature, galvanic skin response, and the like. As used in this disclosure, a "cutaneous phenomenon" is an occurrence that relates to, or is in anyway associated with, skin. Exemplary cutaneous phenomenon includes, without limitation, skin temperature, electrical conductivity of skin, skin moisture, galvanic skin response and the like.

Still referring to FIG. 1, in some embodiments, physiological parameter sensor helmet 100 may include at least a cutaneous sensor 116 that includes a skin galvanic sensor 120. Skin galvanic sensor 120 may be configured to detect a skin galvanic response as a function of a cutaneous electrical characteristic. As used in the current disclosure, "galvanic skin response" (GSR) is a cutaneous phenomenon that causes variation in the electrical characteristics of the skin or the cutaneous phenomenon's representation as a cutaneous parameter. GSR may also refer to a recorded electrical resistance between two electrodes when a very weak current is steadily passed between them. GSR may also be referred to as skin conductance, galvanic skin response (GSR), electrodermal response (EDR), psychogalvanic reflex (PGR), skin conductance response (SCR), sympathetic skin response (SSR), and skin conductance level (SCL). Under GSR, skin resistance may vary with the state of sweat glands in the skin. Sweating may be controlled by the sympathetic nervous system, and skin conductance may be an indication of psychological or physiological arousal. If a sympathetic branch of an autonomic nervous system is highly aroused, then sweat gland activity may increase. This in turn increases skin conductance. In this way, skin conductance may be a measure of emotional and sympathetic responses. GSR may represent a relationship between emotional arousal and sympathetic activity, although electrical change alone may not identify which specific emotion is being elicited. These autonomic sympathetic changes may alter sweat and blood flow, which in turn affects GSR. The number of sweat glands varies across the human body, being highest in hand and foot regions. In some embodiments cutaneous sensor 116 may account for the number of sweat glands that are present in a given area. The response of the skin and muscle tissue to external and internal stimuli can cause conductance to vary by several microsiemens. Sensor 117 may detect, transmit, record and/or display these subtle changes. In other embodiments, a skin galvanic sensor 120 may be configured to detect changes between electrodermal resistance and electrodermal potential. A galvanic skin sensor may use a plurality of electrodes; the electrodes may be placed about a distance apart (e.g., an inch apart). In some embodiments, skin galvanic sensor 120 may measure electrodermal resistance between plurality of electrodes. In some embodiments, skin galvanic sensor 120 may measure electrodermal potential between plurality of electrodes. In some embodiments, skin galvanic sensor 120 may measure electrodermal current between plurality of electrodes. In some embodiments, resistance measured by skin galvanic sensor 120 may vary according to emotional state of user. In other embodiments, a galvanic skin senor 120 may further be configured to detect Galvanic skin potential (GSP). GSP refers to potential (e.g., voltage) measured between two electrodes without any externally applied current. GSP may be measured by connecting electrodes to an amplifier. In some cases, GSP may vary with the emotional state of the subject.

Still referring to FIG. 1, in some embodiments of physiological parameter sensor helmet 100, cutaneous sensor 116 may include a skin temperature sensor 124. As used in this disclosure, a "skin temperature sensor" is a device that is configured to detect a skin temperature parameter as a function of a skin temperature. For example, a skin temperature sensor may include RTDs, thermowells, gauges, calibration equipment, nickel and thermocouple alloy, and the like. Skin temperature sensor 124 may be configured to detect at least a skin temperature parameter as a function of at least a skin temperature. As used in this disclosure, a "skin temperature parameter" is a representation of a skin temperature. As used in this disclosure, "skin temperature" is a cutaneous temperature. In some cases, variability in skin temperature may indicate changes in cardiac output. For instance, increased skin temperature may result for increased blood flow which may indicate increased heart rate and user stress. In some cases, physiological parameter sensor helmet 100 may additionally include at least an environmental temperature sensor 128. As used in this disclosure, an "environmental temperature sensor" is a device that is configured to detect an environmental temperature parameter as a function of an environmental temperature. Environmental temperature sensor 128 may be configured to detect an environmental temperature parameter as a function of an environmental temperature. For example, environmental temperature sensor may include thermocouples, RTDs (resistance temperature detectors), thermistors, air temperature sensors, semiconductor based integrated circuits (IC), and the like. As used in this disclosure, an "environmental temperature parameter" is a representation of an environmental temperature. As used in this disclosure, an "environmental temperature" is a thermal characteristic of an environment. In some cases, at least a cutaneous parameter is a function of at least a skin temperature parameter and at least an environmental temperature parameter.

With continued reference to FIG. 1, computing device 104 may be in communication with at least a cutaneous sensor 116. Memory 112 may include instructions. Instructions may be performed by processor 108. Performing instructions may be configure computing device 104 to receive at least a cutaneous parameter from cutaneous sensor 116 and determine at least a user performance parameter as a function of cutaneous parameter. As used in this disclosure, a "user performance parameter" is a representation of human performance. Computing device 104 may determine user performance parameter using any methods and systems described in this disclosure, for example by using a machine learning process as described below.

Still referring to FIG. 1, Helmet 102 may include any user interface described in this disclosure, such as without limitation a headset. Helmet 102 may be in communication with computing device 104. Helmet 102 may be configured to communicate an alert to a user, for example as a function of the user performance parameter. In some cases, helmet 102 may be configured to communicate an alert, for instance to flight crew member. In some cases, a user interface may be configured to communicate alert as a function of likelihood of atelectasis. As used in this disclosure, an "alert" is a communication to a flight crew member. Alert may alternatively be referred to in this disclosure as being or relating to a physiological alarm condition. In some cases, an alert may indicate a warning pertaining to a flight crew member's risk of atelectasis. An alert may be communicated audibly, visually, and/or haptically. In some cases, alert may include a message. As used in this disclosure, a "message" is a communication configured to communicate information. For example, in some cases, a message may communicate a procedure which a user should engage in. Alternatively or additionally, a message may communicate a warning to a user about diminished performance. A message may be communicated visually, audibly, and/or haptically. As used in this disclosure, a "user interface" is a system that is designed and/or configured to facilitate communication between at least a system, such as without limitation a computing device 104, and a user by way of at least an output communicated to the user and/or at least an input communicated from the user. Exemplary non-limiting user interfaces include displays, audio systems, haptic systems, head mounted displays, mice, joysticks, keyboards, and the like. Helmet 102 may be configured to alert flight crew member as a function of likelihood of atelectasis. In some cases, helmet 102 may include headphones, for example over ear headphones including an earcup. Helmet 102 includes a bone conducting transducer 132, for example located within an earcup of a headphone. A "bone conducting transducer," as used in this disclosure, is a device or component that converts an electric signal to a vibrational signal that travels through bone in contact with the device or component to an inner ear of user. The ear of the user may interpret the vibration as an audible signal. Bone-conducting transducer 132 may include, for instance, a piezoelectric element, which may be similar to the piezoelectric element found in speakers or headphones, which converts an electric signal into vibrations. In an embodiment, bone-conducting transducer 132 may be mounted to housing in a position placing it in contact with a user's bone; for instance, where housing includes or is incorporated in an ear cup, housing may place bone-conducting transducer 132 in contact with user's skull just behind the ear, over the sternocleidomastoid muscle. Likewise, where housing includes a headset, mask, or helmet 102, housing may place bone-conducting transducer 132 in contact with a portion of user's skull that is adjacent to or covered by headset, mask, or helmet 102. Additional disclosure related to headphones and bone conducting transducers may be found in U.S. patent application Ser. No. 17/859,483 filed on Apr. 27, 2020, entitled "HUMAN PERFORMANCE OXYGEN SENSOR," the entirety of which is incorporated herein by reference.

Still referring to FIG. 1, in some embodiments, physiological parameter sensor helmet 100, may additionally include instructions that when performed by processor generates an alert parameter as a function of at least a user performance parameter. As used in this disclosure, an "alert parameter" is a parameter an alert and/or alarm related to a physiological condition. In some cases, helmet 102 may be configured to communicate alert as a function of alert parameter. In some cases, generating alert parameter may include using a machine learning model 140, to generate a physiological alarm condition as described further below.

Still referring to FIG. 1, in some embodiments, physiological parameter sensor helmet 100 may include a computing device 104 comprising a machine learning model 140. In some embodiments, determining user performance parameter includes inputting at least a cutaneous parameter into a machine learning model 140 and generating, using the machine learning model 140, at least a user performance parameter. Machine learning model 140 may include any machine learning model described in this disclosure. In some cases, computing device 104 may be further configured, for instance with memory-stored instructions, to train machine learning model 140. For example, computing device 104 may be configured to input training data into machine learning process, such as without limitation a machine learning algorithm. Machine learning process may include any machine learning process described in this disclosure, such as without limitation a machine learning algorithm. Training data may include any training data described in this disclosure, for instance training data may include cutaneous parameters correlated with human performance parameters. Training data may include historical cutaneous parameters correlated with human performance parameters and/or modeled or analytically-derived correlations. Computing device 104 may be further configured to train machine learning model 140 using machine learning process and training data.

Still referring to FIG. 1, physiological parameter sensor helmet 100 includes at least a physiological sensor 144 installed in helmet 102 and in communication with computing device 104. As used in this disclosure, a "physiological sensor" is a device configured to detect a physiological parameter as a function of a physiological state. Physiological sensor 144 may be configured to detect at least a physiological parameter as a function of a physiological state. In some cases, computing device 104 may be further configured to determine at least a user performance parameter as a function of physiological parameter. Physiological sensor 144 may include at least a sensor. In an embodiment, sensor may include a baroreceptor, temperature sensor, brain activity sensors, pressure sensors, skin sensors, heart rate sensor, blood pressure sensor, sweat sensor, resistance sensor, voltage sensor, multimeters, and the like. As used in this disclosure, a "sensor" is a device that is configured to detect information as a function of a phenomenon; in some cases, a sensor may also transmit the detected information. For example, in some cases a sensor may transduce a detected phenomenon, such as without limitation, current, speed, direction, force, torque, moisture, temperature, pressure, geographic location, the physical state of the user, and the like, into a sensed signal. Sensor may include one or more sensors which may be the same, similar, or different. Sensor may include one or more sensor suites with sensors in each sensor suite being the same, similar, or different. Physiological sensor 144 may be configured to detect at least a physiological parameter. As used in the current disclosure, a "physiological parameter" includes detection of any datum describing a physiological state of user. As used in the current disclosure, a "physiological state" is a physical condition associated with the user. The physiological state may be associated with a data element describing the users physical or mental health.

Still referring to FIG. 1, at least a physiological sensor 144 may include a hydration sensor; hydration sensor may determine a degree to which a user has an adequate amount of hydration, where hydration is defined as the amount of water and/or concentration of water versus solutes such as electrolytes in water, in a person's body. Hydration sensor may use one or more elements of physiological data, such as sweat content and/or hematological parameters detected without limitation using plethysmography, to determine a degree of hydration of a user; degree of hydration may be associated with an ability to perform under various circumstances. For instance, a person with adequate hydration may be better able to resist the effects of hypoxemia in high-altitude and/or high-G for longer or under more severe circumstances, either because the person's body is better able to respond to causes of hypoxemia and delay onset, or because the person is better able to cope with diminished blood oxygen; this may be true of other conditions and/or physiological states detected using at least a physiological sensor 144, and may be detected using heuristics or relationships derived, without limitation, using machine learning and/or data analysis as set forth in further detail below.

Still referring to FIG. 1, physiological sensor 144 may include a volatile organic compound (VOC) sensor. VOC sensor may sense VOCs, including ketones such as acetone; a user may emit ketones in greater quantities when undergoing some forms of physiological stress, including without limitation hypoglycemia resulting from fasting or overwork, which sometimes results in a metabolic condition known as ketosis. As a result, detections of higher quantities of ketones may indicate a high degree of exhaustion or low degree of available energy; this may be associated with a lessened ability to cope with other physiological conditions and/or parameters that may be detected by or using at least a physiological sensor 144, such as hypoxemia, and/or environmental stressors such as high altitude or G-forces. Such associations may be detected or derived using data analysis and/or machine learning as described in further detail below. In some embodiments, physiological sensor 144 may include an oxygen hose of a mobile respiratory assembly such as a respiration assembly used by a pilot in an aircraft. An "oxygen hose," as used in this disclosure, is device configured to allow air flow to a user. A "mobile respiratory assembly," is a structure containing components configured to deliver gases to a user and receive gases from a user. For example, the oxygen hose may deliver oxygen to the user to inhale and remove carbon dioxide exhaled from the user. The respiratory assembly may additionally include an oxygen mask, T bayonet receivers, a corrugated hose, oxygen tank, and the like. The sensor array may be configured to detect a gas concentration level. Gas concentration level may include a concentration level of carbon dioxide, which may be sensed directly and/or by detection of a related compound such as $H_2$, where a "related compound" is a compound, whose concentrations may be related mathematically to $CO_2$ concentrations (e.g., they may be proportional to one another). Gas concentration level may include a volatile organic compound (VOC) level. Gas concentration level may include an oxygen level.

Still referring to FIG. 1, at least a physiological parameter may include at least a circulatory parameter, which may include any detectable parameter describing the state of blood vessels such as arteries, veins, or capillaries, any datum describing the rate, volume, pressure, pulse rate, or other state of flow of blood or other fluid through such blood vessels, chemical state of such blood or other fluid, or any other parameter relative to health or current physiological state of user as it pertains to the cardiovascular system. As a non-limiting example, at least a circulatory parameter may include a blood oxygenation level of user's blood. A "blood oxygenation level," a used in this disclosure, in a measurement of the amount of oxygen in blood. In some embodiments, a circulatory parameter may include cranial blood-oxygenation signals. "Cranial blood-oxygenation signals," as used in this disclosure is a measurement regarding brain activity relating to blood oxygen levels. Cranial blood-oxygenation signals may include measurements based on changes in the magnetic properties of hemoglobin that accompany its conversion from oxyhemoglobin to deoxyhemoglobin. Cranial blood-oxygenation signals may also include changes in intravascular oxyhemoglobin concentration in the brain. In some embodiments, cranial blood-oxygenation signals may reflect the differential deoxyhemoglobin content of blood at different levels of neural activity. In some embodiments, blood oxygenation levels and cranial blood-oxygenation signals may include oxygen content, oxygen saturation, partial pressure of oxygen, partial pressure of carbon dioxide, pH, and the like. At least a circulatory parameter may include a pulse rate. At least a circulatory parameter may include a blood pressure level. At least a circulatory parameter may include heart rate variability and rhythm. At least a circulatory parameter may include a plethysmograph describing user blood-flow; in an embodiment, plethysmograph may describe a reflectance of red or near-infrared light from blood. One circulatory parameter may be used to determine, detect, or generate another circulatory parameter; for instance, a plethysmograph may be used to determine pulse oxygen level (for instance by detecting plethysmograph amplitude), pulse rate (for instance by detecting plethysmograph frequency), heart rate variability and rhythm (for instance by tracking pulse rate and other factors over time), and blood pressure, among other things.

Still referring to FIG. 1, at least a physiological parameter may include neural oscillations generated by user neurons, including without limitation neural oscillations detected in the user's cranial region, sometimes referred to as "brainwaves." Neural oscillations include electrical or magnetic oscillations generated by neurological activity, generally of a plurality of neurons, including superficial cranial neurons, thalamic pacemaker cells, or the like. Neural oscillations may include alpha waves or Berger's waves, characterized by frequencies on the order of 7.5-12.5 Hertz, beta waves, characterized by frequencies on the order of 13-30 Hertz, delta waves, having frequencies ranging from 1-4 Hertz, theta waves, having frequencies ranging from 4-8 Hertz, low gamma waves having frequencies from 30-70 Hertz, and high gamma waves, which have frequencies from 70-150 Hertz. Neurological oscillations may be associated with degrees of wakefulness, consciousness, or other neurological states of user, for instance as described in further detail below. At least a sensor may detect body temperature of at least a portion of user's body, using any suitable method or component for temperature sensing.

Still referring to FIG. 1, in some embodiments, physiological sensor 144 may include a neural activity sensor. A neural activity sensor, as used herein, includes any sensor configured to detect electrical or magnetic phenomena generated by neurons, including cranial neurons such as those located in the brain or brainstem. Neural activity sensor may include an electroencephalographic sensor. Neural activity sensor may include a magnetoencephalographic sensor. In an embodiment, neural activity sensor may be configured to detect neural oscillations. At least a sensor may include an eye-tracking sensor, such as one or more cameras for tracking the eyes of user. Eye-tracking sensor may include, as a non-limiting example, one or more electromyographic (EMG) sensors, which may detect electrical activity of eye muscles; electrical activity may indicate activation of one or more eye muscles to move the eye and used by a circuit such as an alert circuit as described below to determine a movement of user's eyeball, and thus its current location of focus.

Still referring to FIG. 1, physiological sensor 144 is configured to measure a plurality of physiological parameters of a user, wherein the plurality of physiological parameters comprises at least a plurality of blood-oxygenation signals as described above (e.g., circulatory parameter, gas concentration, VOC). In some embodiments, physiological sensor 144 may include a near-infrared spectroscopy sensor as described in FIG. 4. In some embodiments, near-infrared spectroscopy sensor may be configured to measure cranial blood-oxygenation signals from the user. The near-infrared spectroscopy sensor may include at least one optical sensor and at least one infrared light emitting diode. physiological sensor is incorporated into helmet 102, thus measuring the wearer's vital oxygenation signals while the user is wearing the helmet 102. Physiological sensor 144 may include a cranial blood oxygen sensor, for example as described in U.S. patent application Ser. No. 17/859,483, entitled "HUMAN PERFORMANCE OXYGEN SENSOR," filed on Apr. 27, 2020, the entirety of which is incorporated in this disclosure by reference. Another exemplary physiological sensor 144 may include an exhalation sensor, for example as described in U.S. Pat. No. 11,172,845, entitled "COMBINED EXHALED AIR AND ENVIRONMENTAL GAS SENSOR APPARATUS," filed Jul. 20, 2020, the entirety of which is incorporated in this disclosure by reference. Yet another exemplary physiological sensor 144 may include an inhalation sensor, for example as described in U.S. patent application Ser. No. 17/333,179, entitled "INHALATION SENSOR APPARATUS FOR MOBILE RESPIRATION EQUIPMENT," filed on May 28, 2021, the entirety of which is incorporated in this disclosure by reference.

Still referring to FIG. 1, in some embodiments, helmet 102 may include a plurality of housings. As used in the current disclosure, a "housing" is a rigid casing that encloses equipment. Housing may be constructed of any material or combination of materials, including without limitation metals, polymer materials such as plastics, wood, fiberglass, carbon fiber, or the like. In an embodiment, housing is shaped to conform to a particular portion of user anatomy when placed on exterior body surface. When placed to so conform, housing may position at least a sensor and/or user signaling device in a locus chosen as described in further detail below. For example, a cutaneous sensor 116 may be mounted within housing, such that the cutaneous sensor 116 is placed in contact with a user's skin during use. For instance, where housing is incorporated in a helmet 102, mask, earcup or headset, housing 204 may be positioned at a particular portion of user's head when helmet 102, mask, earcup or headset is worn, which may in turn position at least a sensor and/or user signaling device at a particular locus on user's head or neck. Headset and housing are discussed in further with respect to FIG. 2.

Still referring to FIG. 1, computing device 104 may be configured to be wirelessly connected to a user device. As used in the current disclosure, a "user device" is an electronic device such as a computing device, smartphone, tablet, laptop, smart watch, fitness tracker, FITBIT, wearable, and the like. In an embodiment a sensor (e.g., cutaneous sensor 116, environmental temperature sensor 128, and/or physiological sensor 144) may be located on or communicative by way of a user device. User device may be connected to computing device 104 using internet, Wi-Fi, Bluetooth, cellular communication, radio communication, satellite communication, and the like. As used in the current disclosure, "Bluetooth" is a short-range wireless technology standard that is used for exchanging data between fixed and mobile devices over short distances. In embodiments, Bluetooth may use UHF radio waves in the ISM bands, from 2.402 GHz to 2.48 GHz, and building personal area networks (PANs). Bluetooth may be used to exchange files between nearby user devices. Bluetooth may be used to connect user devices with headset.

Still referring to FIG. 1, one or more of cutaneous sensor 116, environmental temperature sensor 128, and/or physiological sensor 144 may be communicatively coupled to the computing device 104. As used herein, "communicative coupling" is a process whereby one device, component, or circuit is able to receive data from and/or transmit data to another device, component, or circuit. In an embodiment, communicative coupling includes electrically coupling at least an output of one device, component, or circuit to at least an input of another device, component, or circuit. Communicative coupling may further be performed by creating an optical, inductive, wireless, or other coupling between two or more devices. Communicative coupling may include placing two or more devices in near field communication with one another. Communicative coupling may include configuring two or more devices to send and/or receive signals to or from each other. Communicative coupling may include direct or indirect coupling; for instance, two or more devices may be connected or otherwise communicatively coupled by way of an intermediate circuit. Communicative coupling may be performed via a bus or other facility for intercommunication between elements of a computing device as described in further detail below in reference to FIG. 8. Communicative coupling may include fabrication together on a shared integrated circuit and/or wafer; for instance, and without limitation, two or more communicatively coupled devices may be combined in a single monolithic unit or module.

Still referring to FIG. 1, physiological parameter sensor helmet 100 may include a microphone 148. As used in this disclosure, a "microphone" is any transducer configured to transduce pressure changes to a signal. Microphone 148, according to some embodiments, may include a transducer configured to convert sound into electrical signal. Microphone may be configured to transduce an environmental noise to an environmental noise signal. Exemplary non-limiting microphones include dynamic microphones (which may include a coil of wire suspended in a magnetic field), condenser microphones (which may include a vibrating diaphragm condensing plate), and a contact (or conductance) microphone (which may include piezoelectric crystal material). Microphone 148 may include any microphone for transducing pressure changes, as described above; therefore, microphone 148 may include any variety of microphone, including any of: condenser microphones, electret microphones, dynamic microphones, ribbon microphones, carbon microphones, piezoelectric microphones, fiber-optic microphones, laser microphones, liquid microphones, microelectromechanical systems (MEMS) microphones, and/or a speaker microphone. In some cases, environmental noise may include any of background noise, ambient noise, aural noise, such as noise heard by a user's ear, and the like. Additionally or alternatively, in some embodiments, environmental noise may include any noise present in an environment, such as without limitation an environment surrounding, proximal to, or of interest/disinterest to a user. Environmental noise may, in some cases, include substantially continuous noises, such as a drone of an engine. Alternatively or additionally, in some cases, environmental noise may include substantially non-continuous noises, such as spoken communication or a backfire of an engine. Environmental noise signal may include any type of signal, for instance types of signals described in this disclosure. For instance, an environmental noise signal may include a digital signal or an analog signal.

Still referring to FIG. 1, computing device 104 may be configured to receive environmental noise signal. Computing device 104 may receive environmental noise signal according to any communication method, for instance communication methods described in this disclosure. Computing device 104 may generate a noise-reducing sound signal as a function of environmental noise signal. As used in this disclosure, a "noise-reducing sound signal" is a sound signal that is configured to generate a noise-reducing sound. In some cases, user interface may include a speaker 152. Speaker 152, in some embodiments, may be configured to generate a noise-reducing sound, as a function of noise-reducing sound signal. As used in this disclosure, a "noise-reducing sound" is sound that at least partially destructively interferes with another sound, for example an environmental noise. According to some embodiments, computing device 104 generates noise-reducing sound signal in order to introduce a noise-reducing sound thereby resulting in active noise cancelling (ANC) and/or active noise reduction (ANR). Computing device 104 may generate noise-reducing sound signal by processing environmental sound signal using analog or digital signal processing techniques. For instance, according to some embodiments, environmental noise signal includes environmental soundwaves that represent at least a component of environmental noise 144 and computing device 104 generates noise-reducing sound signal at least in part by generating antiphase soundwaves that are out of phase with the environmental soundwaves. When a speaker 152 generates a noise-reducing sound that includes an antiphase soundwave, the antiphase soundwave may destructively interfere with an environmental soundwave, thereby reducing sound of the environmental soundwave. In some cases, an environmental soundwave may be taken in by a receiver and reproduced by a speaker 152 in the form of sounds having an opposite phase (noise-reducing sound). Means of carrying out said processes may consist of an electrical apparatus and where reception is affected by a microphone 148. Microphone 148 may be used to transform and/or transduce acoustic oscillations into electric oscillations. Microphone 148 may be connected over an amplifier with a speaker 152 (loudspeaker). In some cases, phase opposition can be affected by several means. In case for instance of only one single tune moving in one well defined direction, phase opposition can be affected in a very simple manner by adjusting a distance between microphone 148 and speaker 152. In this case, microphone 148 may be placed between a sound source and a speaker 152, causing sound oscillations to meet first the microphone 148 and then the speaker 152. Consequently, in some cases, two different kinds of oscillations are present in the speaker 152, the one representing the sound oscillation of the tune, moving with normal sound velocity, the other representing a wave advanced with respect to the first wave by electrical means between the microphone and the speaker 152 and reproduced by the speaker 152. Phase opposition can be affected by suitably adjusting a distance between microphone 148 and speaker 152. In order to silence acoustic vibrations of any shape within a certain range, microphone 148 and loudspeaker 152 may be suitably placed close to each other in such a way that the oscillations coming from a certain point will meet the microphone 148 and the loudspeaker 152 at substantially the same time. Additional disclosure related to microphones, speakers, and noise-cancellation processing may be found in U.S. patent application Ser. No. 17/333,179, entitled "SYSTEMS AND METHODS FOR DYNAMIC NOISE REDUCTION," filed on May 28, 2021, the entirety of which is incorporated in this disclosure by reference.

Still referring to FIG. 1, speaker 152 may be understood as acting in a manner opposite of microphone. As used in the current disclosure, a "speaker" is an apparatus that converts electrical impulses into sound. In some embodiments, a speaker may be referred to as a loudspeaker. In some embodiments, speaker 152 may be a transducer configured to convert any sound signal into a sound. For instance, an alert, message, or user communication may be represented as a sound signal and audibly communicated to a user with speaker 152. Speaker 152 may be an electroacoustic transducer that converts an electrical audio signal into a corresponding sound. Speaker 152 may include any variety of speakers including, but not limited to dynamic speakers. Dynamic speakers may operate on according to a same basic principle as a dynamic microphone, but in reverse, to produce sound from an electrical signal. When a signal (e.g., an alternating current electrical audio signal) is applied to a dynamic speaker's voice coil, the voice coil is driven rapidly back and forth due to Faraday's law of induction. A voice coil may include a coil of wire suspended in a circular gap between the poles of a permanent magnet. Voice coil's rapid movements may cause a diaphragm (e.g., a conically shaped diaphragm) attached to the voice coil to move back and forth, as well. Movement of diaphragm may push air proximal the diaphragm thereby creating sound waves. In some cases, a speaker may include multiple speakers, referred to as drivers. Drivers made for reproducing high audio frequencies may be referred to as tweeters, those for middle frequencies are called mid-range drivers, and those for low frequencies may be called woofers. Extremely low frequencies (e.g., between about 17 Hz and about 100 Hz) may be reproduced by separate subwoofers physically independent from speaker, for example to limit interference. According to some embodiments, speaker 152 may be selected according to one or more specifications, including without limitation speaker or driver type, physical size, nominal power, impedance, enclosure type, number of drivers, class (e.g., Class 1-Class 4), crossover frequencies, frequency response, Thiele parameters, sensitivity, and/or maximum sound pressure level.

Still referring to FIG. 1, in some embodiments, signals may be processed. For instance, signals may include sound signals associated with microphone 148 and/or speaker 152. Alternatively or additionally signals may include sensor signals associated with one more sensors (e.g., cutaneous sensor 116, environmental temperature sensor 128, physiological sensor, 144, and the like). Exemplary methods of signal processing may include analog, continuous time, discrete, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which varying continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point and floating-point, real-valued, and complex-valued, multiplication and addition. Digital signal processing may additionally operate circular buffers and lookup tables. Further non-limiting examples of algorithms that may be performed according to digital signal processing techniques include fast Fourier transform (FFT) implemented using hardware and/or software configurations, finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal, for example by using any signal filtering method described in this disclosure, including without limitation signal characteristic filtering and/or signal characteristic pass-through. In some cases, signal analysis (i.e., processing) may include non-linear filtering of signals. An exemplary non-limiting technique for non-linear filtering may include homographic filtering; homographic filtering may include a non-linear mapping of a signal from an original domain to new domain, filtering according to linear processing in the new domain, and then a mapping back to the original domain. In some cases, homographic analysis may be performed to find a cepstrum of a signal. A cepstrum may include a signal transformed into a log-spectrum domain. An exemplary cepstrum is a power spectrum. Power spectrum of a signal may be found thus:

$$C_p = |\{\mathcal{F}^{-1}(|\mathcal{F}\{f(t)\}|^2)\}|^2$$

where, $F^{\wedge}(-1)$ is inverse Fourier transform, F is Fourier transform, and f(t) is signal in time domain. In some cases, cepstrum may include any of an autocepstrum, kepstrum, and the like.

Still referring to FIG. 1, in some cases, feature extraction may be performed on an individual segment. Signal features may be found through any known means, including for example pattern-recognition, scale-invariant feature transform (SIFT) feature detection, and the like. An exemplary set of resources available for signal processing include MIRToolbox from Matlab of Natick, Massachusetts. In some cases, feature detection may be performed by way of machine-learning processes. Signal features may be derived from any signal variables. Signal variables can be of any time, including without limitation: time-domain variables (e.g., number of peaks, Root Mean Squared (RMS) energy, number of onsets, rhythmic parameters, zero-crossing rate, and the like), spectral variables (e.g., rolloff frequencies, brightness, spectral statistics, and the like), and cepstral variables (e.g., Mel Frequency Cepstral Coefficient, power cepstrum statistics, and the like). In some cases, cepstral variables may be used to determine at least a component of a signal, for instance at least a component related to a fundamental frequency of human speech. In some cases, component recognition within a signal may be performed using supervised, unsupervised, or semi-supervised machine-learning processes trained with training representative of the component sought to be recognized. For instance, a machine-learning process may be employed to determine a language component within a signal, and the machine-learning process may be trained using training data included language, for instance without limitation audiobooks. In some cases, a machine-learning process may be trained using general data for global functionality; alternatively or additionally, in some cases, a machine-learning process may undergo a training within a certain context or environment for environment specific, or local, functionality. Machine-learning processes may be performed in any domain, for example domains described within this application, such as without limitation time-domain, spectral-domain, cepstral-domain, wavelet-domain, and the like.

With continued reference to FIG. 1, human performance affects, such as without limitation distractibility, loss of focus and the like, may be correlated to cutaneous parameters and/or physiological characteristics, for instance without limitation galvanic skin response, skin temperature, cranial blood oxygenation, eye tracking information, and the like. In some cases, physiological parameter sensor helmet 100 may be used for correlating measured cutaneous parameters and/or physiological parameters and associating an estimated human performance from these data. For instance computing device 104 may determine at least a user performance parameter as a function of at least a cutaneous parameter and/or physiological parameter. Computing device may determine and communicate an alert to a user as a function of performance parameter. In some cases, an alert may be communicated by way of a notification.

Still referring to FIG. 1, computing device 104 is configured to receive the plurality of physiological parameters from the at physiological sensor 144. Physiological sensor 144 may detect at least a physiological parameter and transmit an electrical signal as a result of the detection to computing device; transmission of an electrical signal, as used herein, includes any detectable alternation of an electrical parameter of an electrical circuit incorporating at least a physiological sensor 144. For instance, at least a physiological sensor 144 may increase or reduce the impedance and/or resistance of a circuit to which at least a physiological sensor 144 is connected. At least a physiological sensor 144 may alter a voltage or current level, frequency, waveform, amplitude, or other characteristic at a locus in circuit. Transmission of an electrical signal may include modulation or alteration of power circulating in circuit; for instance transmission may include closing a circuit, transmitting a voltage pulse through circuit, or the like. Transmission may include driving a non-electric signaling apparatus such as a device for transmitting a signal using magnetic or electric fields, electromagnetic radiation, optical or infrared signals, or the like.

Still referring to FIG. 1, computing device is configured to generate a health profile 156 as a function of the plurality of physiological parameters. A "health profile," as used in this disclosure, is a data structure containing at least analyzed physiological parameters of a user. Health profile 156 may contain analytical related to cutaneous, physiological, and environmental parameters. In some embodiments, health profile 156 may contain a plurality of physiological alarm conditions as described further below. A "physiological alarm condition," as used in this disclosure, is an alert related to a physiological condition of a user. For example, health profile 156 may contain detection of a health and/or cognitive status of a user, including hypocapnia and/or hypercapnia detection. Health profile 156 may contain detection a dangerous level of one or more gases, fatigue, hypoxia, and/or atelectasis and the like. Health profile 156 may be generated utilizing a machine-learning model as described further below. Computing device 104 may generate a notification as a function of health profile 156. As used in the current disclosure, a "notification" is a form of notifying or informing of the user. A notification may be an audio, visual, or haptic. In embodiments, a verbal notification may play through speaker 152. In other embodiments, a speaker 152 may play a noise reducing sound while a verbal announcement is being made. Computing device 104 may periodically sample data from at least a sensor; in a non-limiting example, data may be sampled 75 times per second. In an embodiment, a notification is generated upon detection of any signal at all from at least a sensor that may indicate problematic or otherwise crucial situation. Alternatively or additionally, computing device 104 may be further configured to generate a notification as a function of a physiological alarm condition. In an embodiment, a physiological alarm condition may include any physiological condition of user that may endanger a user or impair user's ability to perform an important task; as a non-limiting example, if user is flying an aircraft and user's physiological condition is such that user is unable to concentrate, respond rapidly to changing conditions, see or otherwise sense flight controls or conditions, or otherwise successfully operate the aircraft within some desired tolerance of ideal operation, a physiological alarm condition may exist, owing to the possibility of inefficient or dangerous flight that may result. Similarly, if user's physiological condition indicates user is experiencing or about to experience physical harm, is losing or is about to lose consciousness, or the like, a physiological alarm condition may exist. Physiological alarm condition may be determined as a function of performance parameter, such as by using a machine learning process like a classifier.

Still referring to FIG. 1, in some embodiments, detection of a physiological alarm condition may include comparison of one or more of a cutaneous parameter, a physiological parameter, and a performance parameter to a threshold level. For instance, and without limitation, detection of the physiological alarm condition may additionally include determination that a parameter falls below a threshold level; as an example, blood oxygen levels below a certain cutoff indicate an imminent loss of consciousness, as may blood pressure below a certain threshold. In a further non-limiting example, GSR may demonstrate that user is having a severe emotional response. Comparison to threshold may include comparison of a parameter to a value stored in a database, which may be a digitally stored value; alternatively or additionally comparison may be performed by analog circuitry, for instance by comparing a voltage level representing at least a physical parameter to a reference voltage representing the threshold, by means of a comparator or the like. Threshold may represent or be represented by a baseline value.

Still referring to FIG. 1, detection of physiological alarm condition may include comparing one or more of a cutaneous parameter, a physiological parameter and a performance parameter to at least a baseline value and detecting the physiological alarm condition as a function of the comparison. At least a baseline value may include a number or set of numbers representing normal or optimal function of user, a number or set of numbers representing abnormal or suboptimal function of user, and/or a number or set of numbers indicating one or more parameters demonstrating a physiological alarm condition. At least a baseline value may include at least a threshold as described above. In an embodiment, at least a baseline value may include a typical user value for one or more physiological parameters. For example, and without limitation, at least a baseline value may include a blood oxygen level, blood pressure level, pulse rate, variation in the electrical characteristics of the skin, or other circulatory parameter, or range thereof, consistent with normal or alert function in a typical user; at least a baseline value may alternatively or additionally include one or more such values or ranges consistent with loss of consciousness or impending loss of consciousness in a typical user. This may include loss of consciousness my overheating, severe emotional response, or overexertion. Similarly, at least a baseline value may include a range of neural oscillations typically associated in users with wakeful or alert states of consciousness, and/or a range of neural oscillations typically associated with sleeping or near-sleeping states, loss of consciousness or the like. Computing device 104 may receive a typical user value and using the typical user value as the baseline value; for instance, alert circuit may have typical user value entered into memory of Computing device 104 by a user or may receive typical user value over a network or from another device. At least a baseline value may be maintained in any suitable data structure, including a table, database, linked list, hash table, or the like.

Still referring to FIG. 1, health profile 156 including a physiological alarm condition may be generated using a physiological machine learning model 140. In embodiments, a physiological machine learning model may include a classifier 136, which may be consistent with the classifier disclosed with reference to FIG. 3. Inputs to the to the machine learning model may include a plurality of one or more of cutaneous parameters, physiological parameters, and/or performance parameters correlated to one or more of performance parameters, physiological alarms conditions, baselines for the user, and the like. The output of the machine learning model is health profile 156 including one or more of a performance parameter and/or a physiological alarm condition. Physiological machine learning model may by trained using physiological training data. Physiological training data is a plurality of data entries containing a plurality of inputs that are correlated to a plurality of outputs for training a computing device 104 by a machine-learning process. Training data may include any combination of physiological parameters, cutaneous parameters, performance parameters, examples of physiological alarms conditions, past physiological alarms conditions, baselines for the user, and the like. Training data may include correlations between cutaneous parameter and performance parameter. "Past," refers to the fact that the data was collected prior to the current physiological alarm condition is generated. Training data may be stored in a database, such as a training data database, or remote data storage device, or a user input or device.

Still referring to FIG. 1, in some embodiments, training data may be classified for example, by user, by user cohort, or the like. In some cases, a typical user value may include a user value matched to one or more demographic facts about user. For instance, a pulse rate associated with loss of consciousness in a first cohort may not be associated with loss of consciousness in a second cohort, or vice-versa; where user is the first cohort, the former pulse rate may be used as a baseline value for pulse rate. Baseline value may similarly be selected using a typical value for persons matching user's age, sex, height, weight, degree of physical fitness, physical test scores, ethnicity, diet, or any other suitable parameter. Typical user baseline value may be generated by averaging or otherwise aggregating baseline values calculated per user as described below; for instance, where each user has baseline values established by collection of cutaneous and/or physiological parameters using devices such as physiological parameter sensor helmet 100, such values may be collected, sorted or classified according to one or more demographic facts, and aggregated to produce a typical user baseline value to apply to user.

With continued reference to FIG. 1, plurality of cutaneous parameters, plurality of physiological parameters, plurality of performance parameters, and/or user-entered data may be aggregated, either independently or jointly. For instance, physiological parameter sensor helmet 100 may calculate an average level, for one or more parameters of at least a cutaneous parameter, associated with normal or optimal function, health, or performance of user; a standard deviation from the average may also be calculated. This may be used, e.g., to generate a notification indicating that, for instance, a given cutaneous parameter has recently shifted more than a threshold amount from its average value. Threshold amount may be determined based on amounts by which a typical user may deviate from average amount before experiencing discomfort, loss of function, or loss of consciousness. Threshold amount may be set as some multiple of standard deviations, as calculated from sensed cutaneous parameter; for instance, two or more standard deviations from an average value for a given detected cutaneous parameter may trigger an alarm.

Alternatively or additionally, and still referring to FIG. 1, aggregation may include aggregation of relationships between two or more parameters. For instance, and without limitation, aggregation may calculate a relationship between a physiological parameter and a cutaneous parameter; this relationship may be calculated, as a non-limiting example, by selecting a first parameter as a parameter associated with a desired state for the user and a second parameter known or suspected to have an effect on the first parameter. For example, first parameter may be blood oxygen level, and second parameter may be blood pressure, such as localized blood pressure in a cranial region; a reduction in cranial blood pressure may be determined to be related to a reduction in cranial blood oxygen level, which in turn may be related to loss of consciousness or other loss of function in user or in a typical user. As another example, aggregation may calculate a relationship between a physiological parameter and an environmental parameter. For example, blood oxygen level may be inversely related to an amount of acceleration or G force a user is experiencing in an aircraft; this relationship may be directly calculated from those two values, or indirectly calculated by associating the amount of acceleration or G force with a degree of decrease in cranial blood pressure, which may then be related to blood oxygen levels. Aggregation may calculate a relationship between one or more of a cutaneous parameter and a physiological parameter and user-entered data; for instance, people observing user may note losses of performance or apparent function at times associated with a certain parameter values. The relationships may be between combinations of parameters: for instance, loss of function may be associated with an increase in G forces coupled with a decrease in pulse rate, or a decrease in blood oxygen coupled with a decrease in alpha waves, or the like.

Still referring to FIG. 1, computing device 104 may be programmed to produce a variety of notifications, which may correspond to various physiological alarm condition and/or contexts. Possible notifications may be, but are not limited to imminent unconsciousness, substandard oxygenation, erratic pulse, optimum oxygenation, and/or any other suitable notification, while maintaining the spirit of the present invention. Each such notification may have a distinct pattern of audible, visual, and/or textual notifications; each notification may include, for instance, an audible or textual warning or description of a physiological alarm condition. Any of the above user-signaling devices and/or signals may be used alone or in combination; for instance, a signal to user may include an audio signal produced using a bone-conducting transducer 132, a verbal warning message output by an audio output device, and a visual display of an image or text indicating the physiological alarm condition. Persons skilled in the art, upon reviewing the entirety of this disclosure, will be aware of various combinations of signaling means and/or processes that may be employed to convey a signal to user. In an embodiment, in addition to transmitting an alarm to user signaling device, alert circuit may transmit a signal to one or more automated vehicular controls or other systems to alleviate one or more environmental parameters contributing to physiological alarm condition. For instance, and without limitation, an automated aircraft control may receive a notification of hypoxia while a motion sensor indicates high acceleration; aircraft control may reduce acceleration to alleviate the hypoxia. Persons skilled in the art, upon reviewing the entirety of this disclosure, may be aware of various additional ways in which automated systems may act to alleviate a physiological alarm condition as described herein.

Figure 2A:
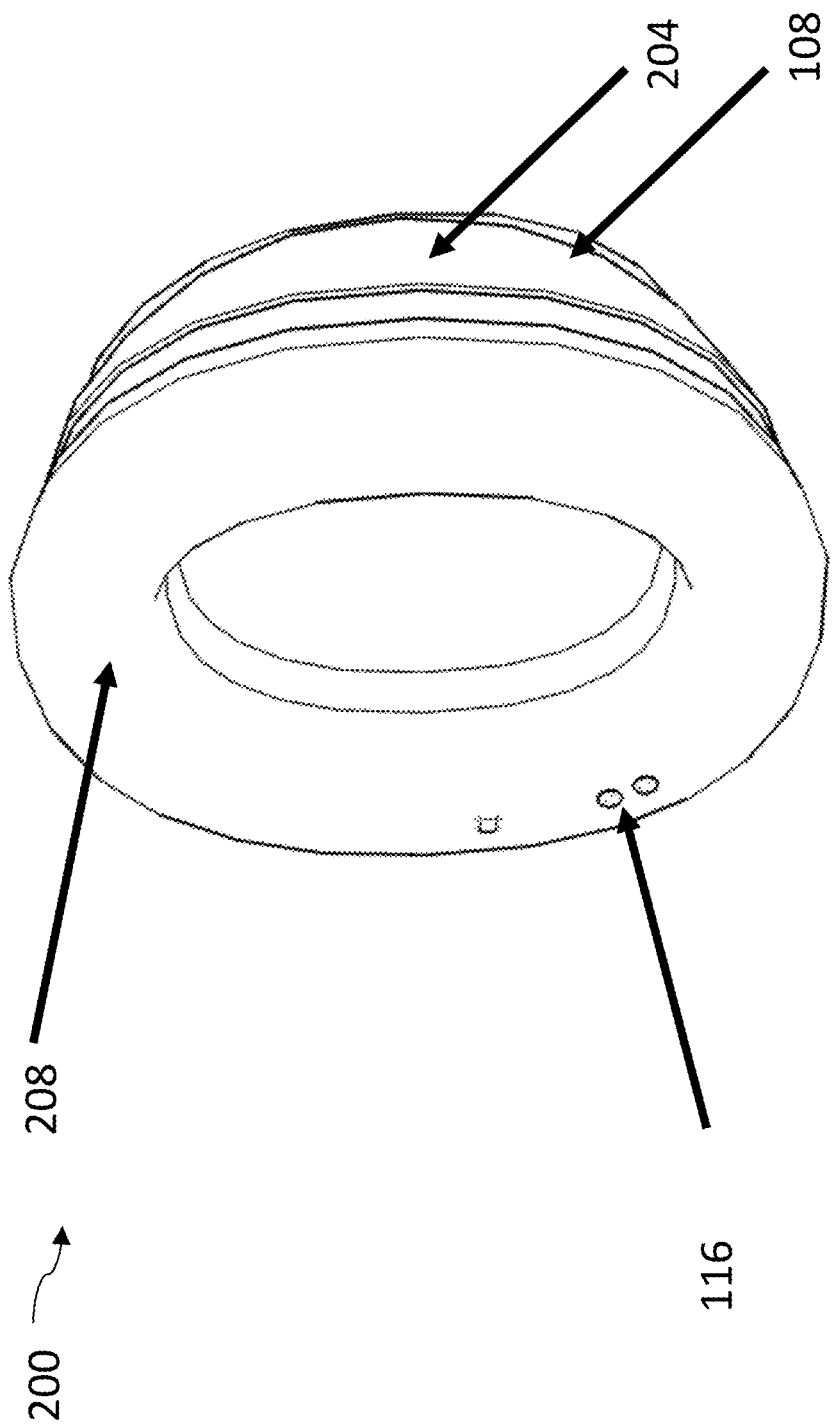
FIG. 2A is an exemplary embodiment of a perspective view of a headset with physiological parameter measurement capabilities.
Figure 2B:
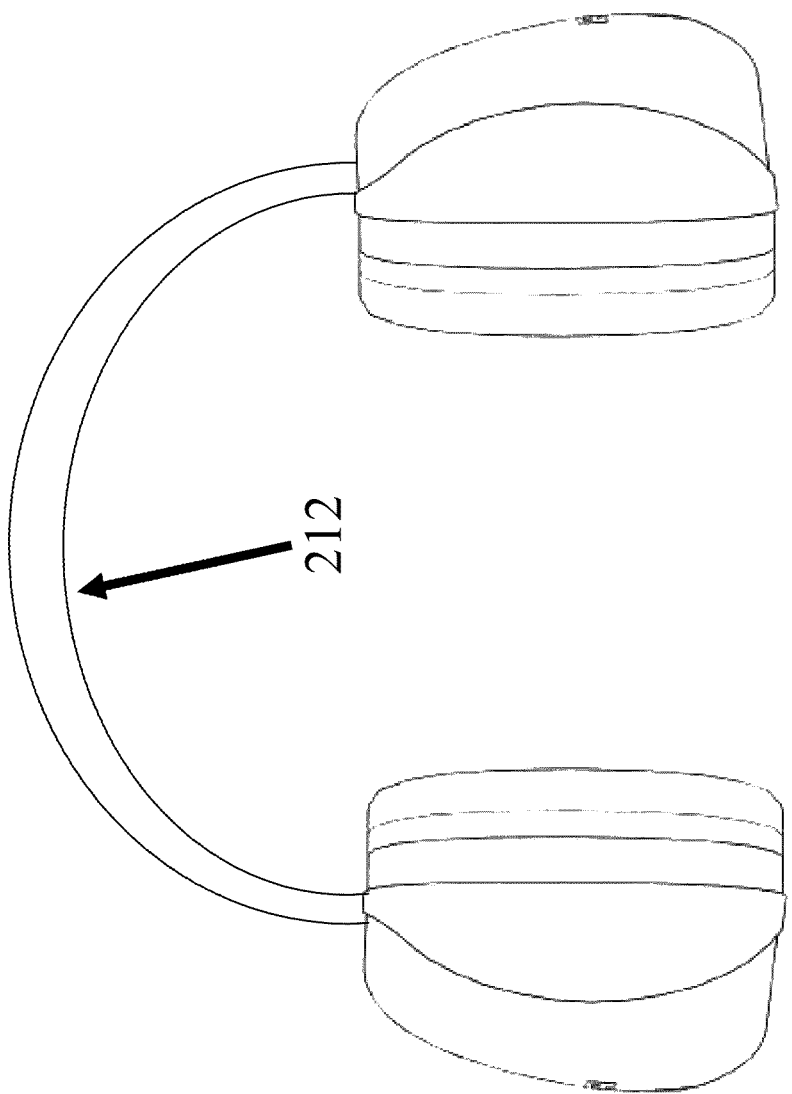
FIG. 2B is an exemplary embodiment of a front view of a headset with physiological parameter measurement capabilities.
Figure 2C:
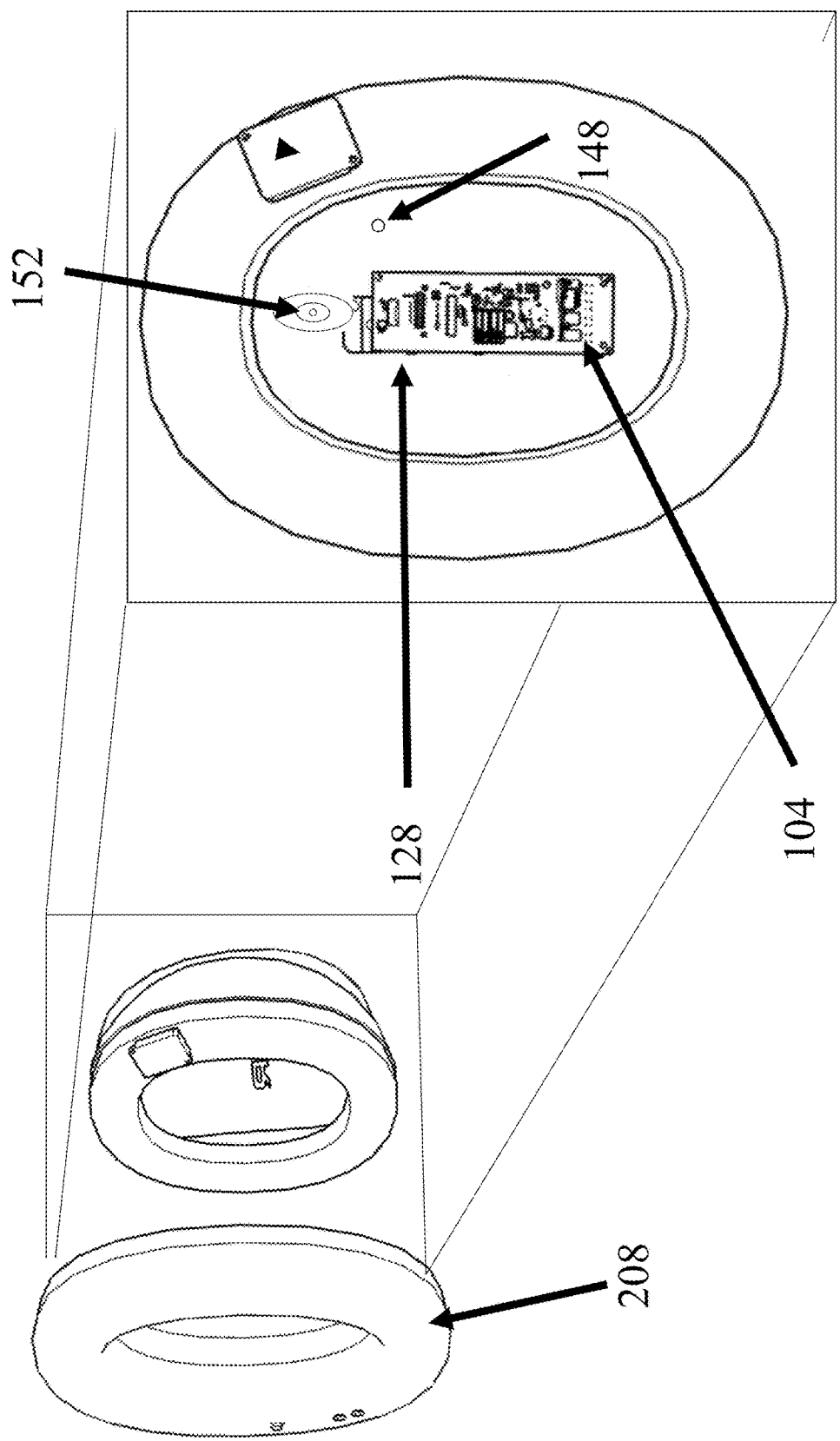
FIG. 2C is an exemplary embodiment of a perspective view of a headset with physiological parameter measurement capabilities.

Referring now to FIGS. 2A-C, an exemplary embodiment of a perspective view of a headset with physiological parameter measurement capabilities is illustrated in FIG. 2A. An exemplary embodiment of a Front view of a headset with physiological parameters measurement capabilities is illustrated in FIG. 2B. An exemplary embodiment of a perspective view of a headset with physiological parameters measurement capabilities is illustrated in FIG. 2C.

Still referring to FIGS. 2A-C, one or more of cutaneous sensor 116, environmental temperature sensor 128, and/or physiological sensor 144 may be attached to a housing 204. In an embodiment, attachment to housing may include mounting on an exterior surface of housing or seal. In some embodiments a cutaneous sensor 116 may be incorporated within housing 204. A sensor may additionally be electrically connected to another element within housing 204, or the like. Alternatively or additionally, physiological sensor 144 may include a sensor that is not attached to housing 204 or is indirectly attached via wiring or the like. As a non-limiting example, at least a sensor and/or one or more components thereof may be coupled to the substantially pliable seal 208. In an embodiment, physiological sensor 144 may be contacting exterior body surface; this may include direct contact with the exterior body surface, or indirect contact for instance through a portion of seal 208 or other components of physiological parameter sensor helmet 100. As a non-limiting example of placement of physiological sensor 144, and as illustrated for exemplary purposes in FIG. 2, physiological sensor 144 may include a sensor mounted on an edge of an earcup, and so positioned that placement of earcup over user's ear places sensor in contact with user's skin just behind the ear at a local skeletal eminence. Similarly, where housing 204 includes a mask as described above, a sensor of physiological sensor 144 may be disposed within mask at a location that, when mask is worn, places sensor against a forehead of user.

Still referring to FIG. 2A, Housing 204 may include a rigid outer shell 204. Rigid outer shell 204 may, for instance, protect internal elements of headset 200 from damage, and maintain them in a correct position on a user's body. Housing 204 and/or rigid outer shell 204 may be inserted on a head of the user, in particular the housing 204 may cover the ears of the user. As a non-limiting example, exterior body surface may be a surface, such as a surface of the head, face, or neck of user, which is wholly or partially covered by helmet 102, as described for example in further detail below. As a further non-limiting example, housing 204 may be formed to have a similar or identical shape to a standard-issue "ear cup" incorporated in an aviation helmet 102, so that housing 204 can replace ear cup after ear cup has been removed. Headset 200 may be the same or substantially the same as headset.

Still referring to FIG. 2A, Seal 208 may be substantially pliable; seal 208 may be constructed of elastomeric, elastic, or flexible materials including without limitation flexible, elastomeric, or elastic rubber, plastic, silicone including medical grade silicone, gel, and the like. Substantially pliable seal 208 may include any combination of materials demonstrating flexible, elastomeric, or elastic properties, including without limitation foams covered with flexible membranes or sheets of polymer, leather, or textile material. As a non-limiting example, substantially pliable seal 208 may include any suitable pliable material for placement over a user's ear, including without limitation any pliable material or combination of materials suitable for use on headphones, headsets, earbuds, or the like. In an embodiment, substantially pliable seal 208 advantageously aids in maintaining housing 204 and/or other components of headset 200 against exterior body surface; for instance, where exterior body surface has elastomeric properties and may be expected to flex, stretch, or otherwise alter its shape or position to during operation, substantially pliable seal 208 may also stretch, flex, or otherwise alter its shape similarly under similar conditions, which may have the effect of maintaining seal 208 and/or one or more components of headset as described in greater detail below. Seal 208 may be attached to housing 204 by any suitable means, including without limitation adhesion, fastening by stitching, stapling, or other penetrative means, snapping together or otherwise engaging interlocking parts, or the like. Seal 208 may be removably attached to housing 204, where removable attachment signifies attachment according to a process that permits repeated attachment and detachment without noticeable damage to housing 204 and/or seal 208, and without noticeable impairment of an ability to reattach again by the same process. As a non-limiting example, substantially pliable seal 208 may be placed on an ear cup of the housing 204.

With continued reference to FIG. 2B, housing 204 may be incorporated into a headset. A headset may include, without limitation, an aviation headset, such as headsets as manufactured by the David Clark company of Worcester Massachusetts, or similar apparatuses. A headset may also be used commercially for recreational use or fitness use. In some embodiments, housing 204 may be a headset; that is, headset may be manufactured by incorporating one or more components into the headset, using the headset as a housing 204. As a further non-limiting example, housing 204 may include a mask; a mask as used herein may include any device or element of clothing that is worn on a face of user during operation, occluding at least a part of the face. Masks may include, without limitation, safety googles, gas masks, dust masks, self-contained breathing apparatuses (SCBA), self-contained underwater breathing apparatuses (SCUBA), and/or other devices worn on and at least partially occluding the face for safety, functional, or aesthetic purposes. Headset may include a mask. Headset 200 may be manufactured by incorporating one or more elements or components of a mask in or on headset 200.

With continued reference to FIG. 2B, a plurality of housings 204 may attach to an element of headgear 212. As used in the current disclosure, a "headgear" is any element worn on and partially occluding a head or cranium of user. In an embodiment, a headgear 212 may attach two housings 108 in a manner which they may be worn around the head. Headgear 212 may wholly or partially occlude user's face and thus also include a mask; headgear 212 may include, for instance, a fully enclosed diving helmet, space helmet, or helmet 102 incorporated in a space suit, or the like. Headgear 212 may include a headband, such as without limitation a headband of a headset. As used in the current disclosure, a "headband" is a band in a horseshoe shape configured to be worn over the top of the head of the user. Additionally, the headband may be connecting piece that runs from a first housing 204 to a second housing 204. The headband may hold them together so that you can comfortably and securely wear the headset 200 on your head. In an embodiment, the housing 204 may be electrically connected by running a wire through the headband. Headgear 212 may include a hat, a helmet 102, a construction "hardhat," a bicycle helmet, or the like.

With continued reference to FIG. 2C, housing 204 may house a plurality of hardware associated with headset including computing device 104, microphone 148, cutaneous sensor 116, physiological sensor 144, skin temperature sensor 124, skin galvanic sensor 120, environmental temperature sensor 128, and speaker 152 may be located within the housing. Housing 204 may be configured mounted to an exterior body surface of a user; exterior body surface may include, without limitation, skin, hair, an interior surface of an orifice such as the mouth, nose, or ears, or the like. Exterior body surface and/or locus may include an exterior body surface of user's head, face, or neck. Environmental temperature sensor 128 may be positioned to within earcup to measure temperature of ambient air proximal skin surface, thereby providing a relative temperature measurement for skin temperature.

With continued reference to FIG. 2C, in an embodiment, at least a cutaneous sensor 116 and/or at least a physiological sensor 144 may contact a locus on the exterior body surface where substantially no muscle is located between the exterior body surface and an underlying bone structure, meaning muscle is not located between the exterior body surface and an underlying bone structure and/or any muscle tissue located there is unnoticeable to a user as a muscle and/or incapable of appreciably flexing or changing its width in response to neural signals; such a locus may include, as a non-limiting example, locations on the upper cranium, forehead, nose, behind the ear, at the end of an elbow, on a kneecap, at the coccyx, or the like. Location at a locus where muscle is not located between exterior body surface and underlying bone structure may decrease reading interference and/or inaccuracies created by movement and flexing of muscular tissue. Physiological sensor 144 may contact a locus having little or no hair on top of skin. Physiological sensor 144 may contact a locus near to a blood vessel, such as a locus where a large artery such as the carotid artery or a branch thereof, or a large vein such as the jugular vein, runs near to skin or bone at the location; in an embodiment, such a position may permit physiological sensor 144 to detect circulatory parameters as described above.

Figure 3:
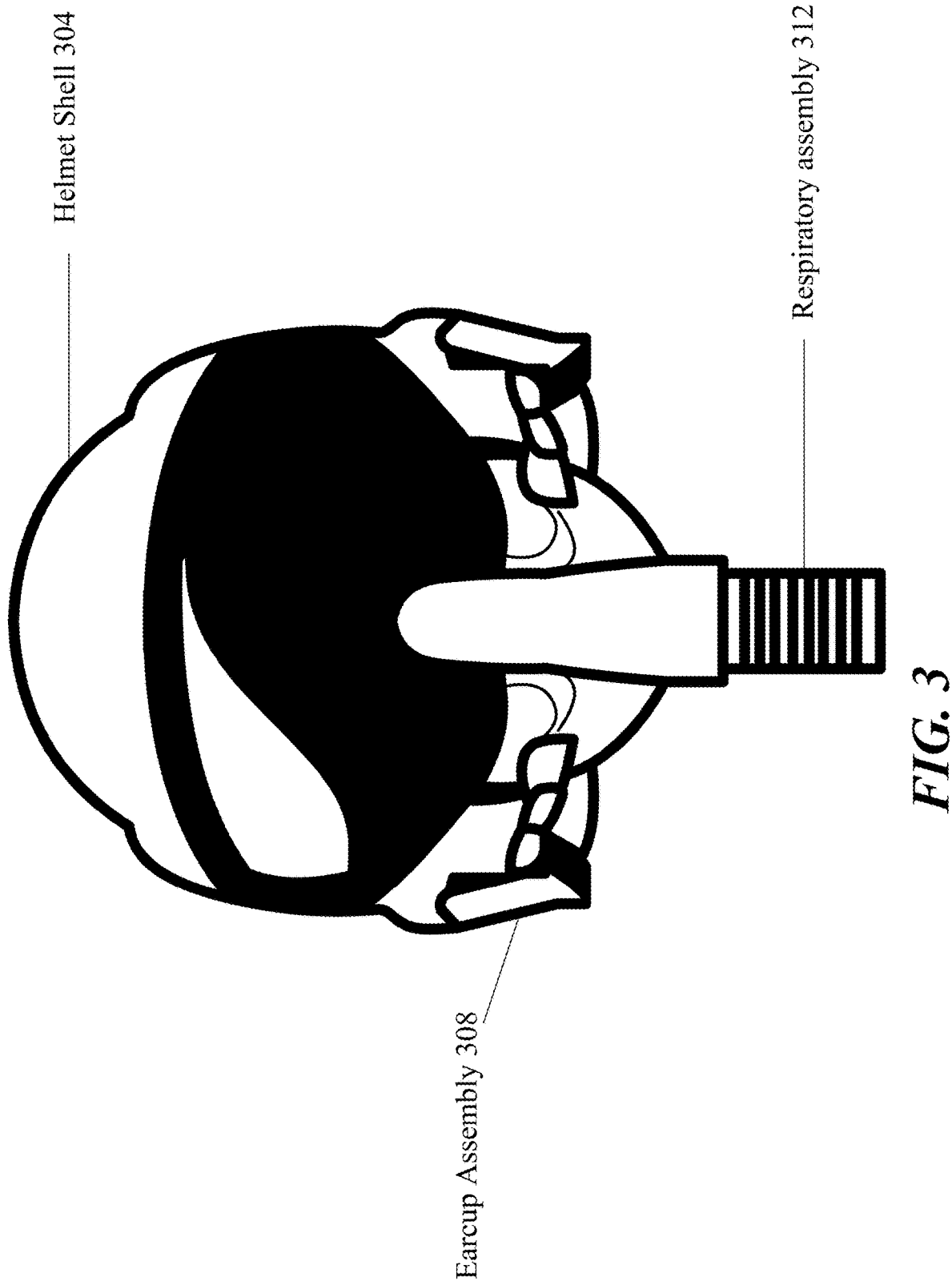
FIG. 3 is a block diagram illustrating an exemplary helmet.

Referring now to FIG. 3, is exemplary embodiment of a helmet 102. Helmet 102 may include components of aviation (pilot) helmet. For example, helmet 102 may include a helmet shell 304, ear cup assembly 308, and respiratory assembly 312. Helmet 102 includes a bone conducting transducer, physiological sensors, and computing device all of which may be located in shell and/or earcup of helmet 102 as described in FIGS. 1-2C. Helmet 102 may include any other devices described throughout this disclosure. For example, a microphone, speaker, and the like. Additionally, helmet 102 may include components as described in described in U.S. patent application Ser. No. 17/859,483, entitled "HUMAN PERFORMANCE OXYGEN SENSOR," filed on Apr. 27, 2020, the entirety of which is incorporated in this disclosure by reference.

Figure 4:
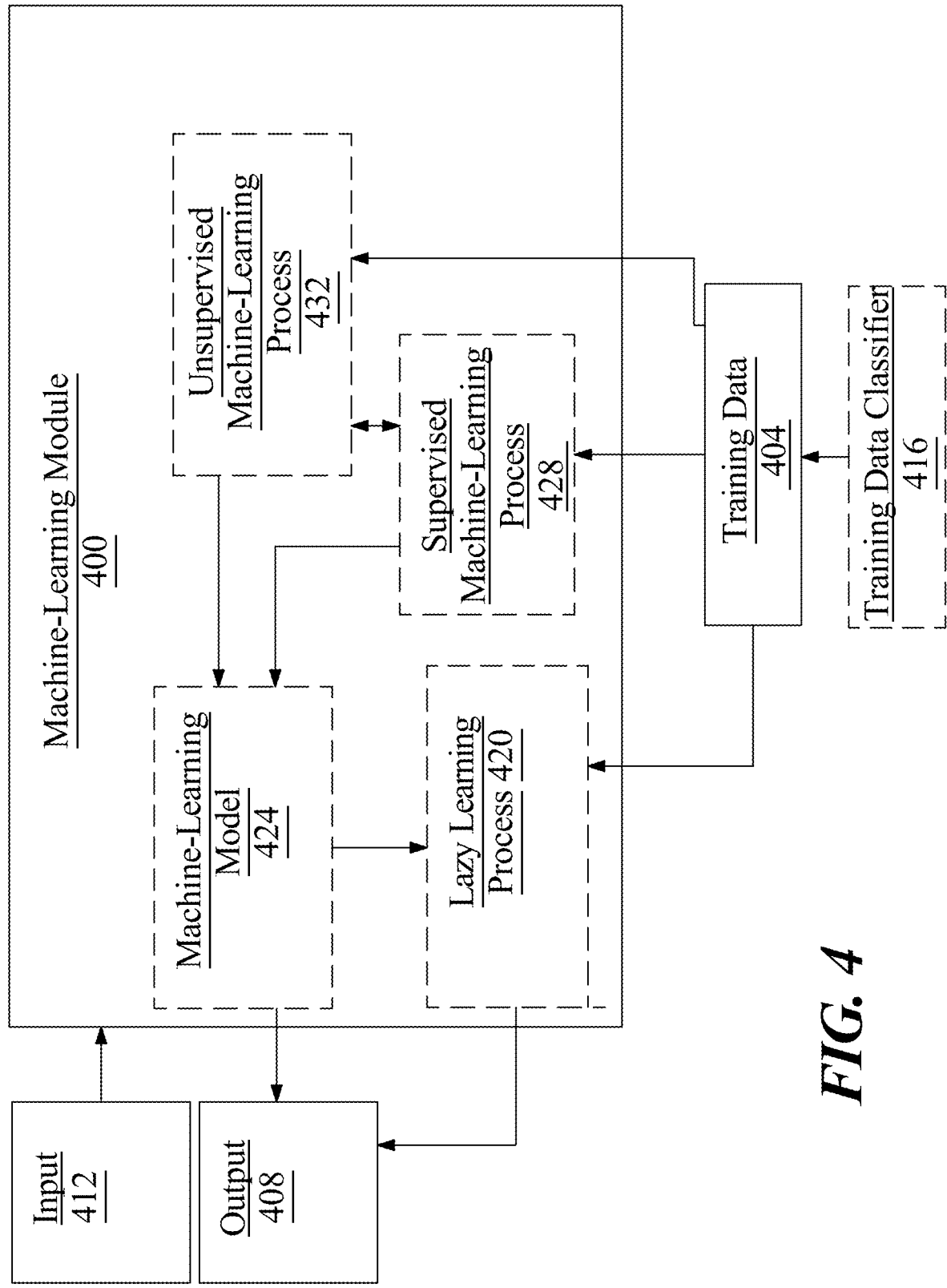
FIG. 4 is a block diagram of an exemplary machine-learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure.

Further referring to FIG. 4, training data may be filtered, sorted, and/or selected using one or more supervised and/or unsupervised machine-learning processes and/or models as described in further detail below; such models may include without limitation a training data classifier 417. Training data classifier 417 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a cutaneous parameter, a physiological parameter, and/or a performance parameter as described above as inputs, performance parameters, and/or alerts as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

Further referring to FIG. 4, machine learning processes may include at least an unsupervised machine-learning processes 442. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

For example, and still referring to FIG. 4, neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, a node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function (p, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above. In an embodiment, and without limitation, a neural network may receive semantic units as inputs and output vectors representing such semantic units according to weights wi that are derived using machine-learning processes as described in this disclosure.

Figure 5:
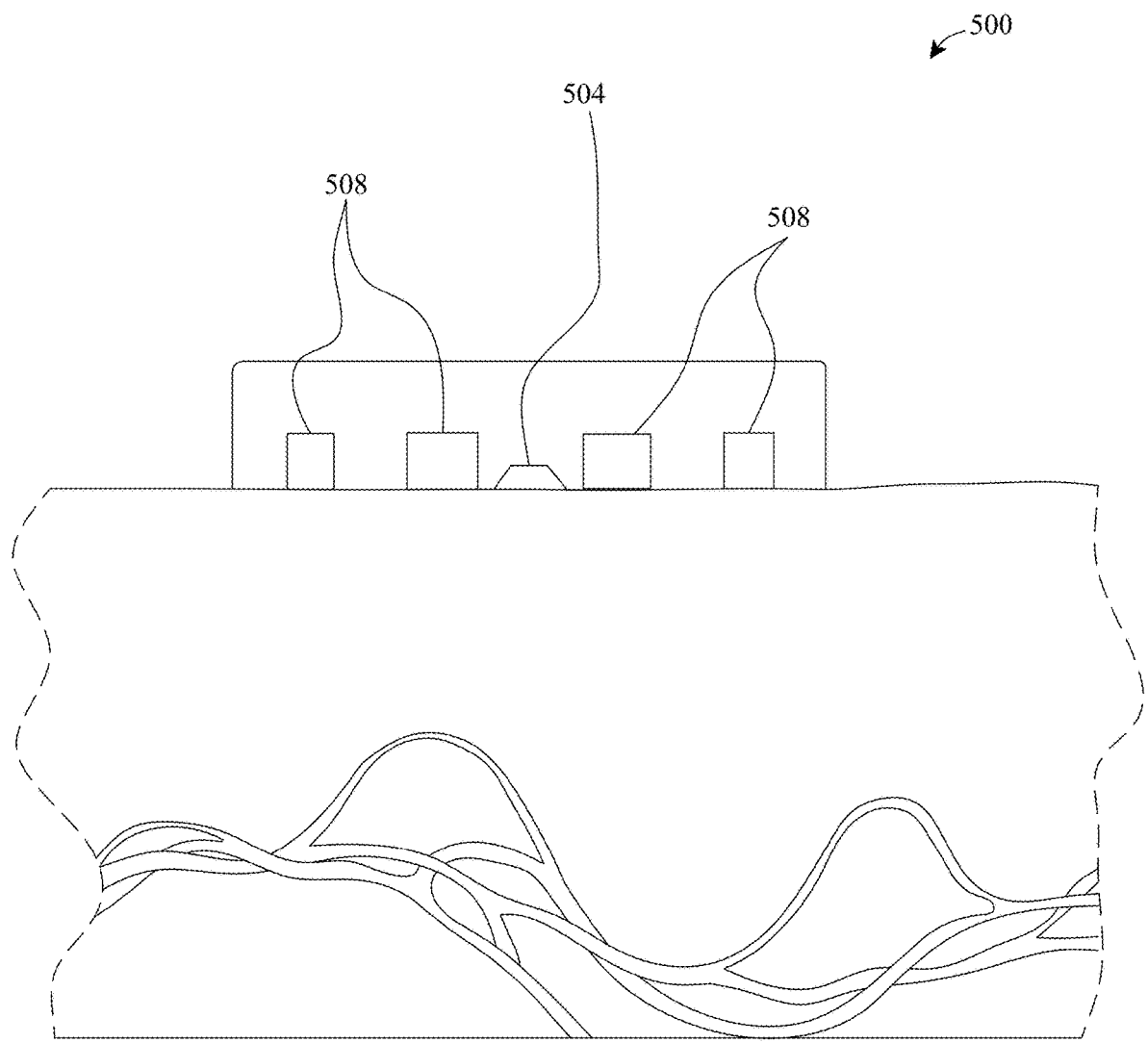
FIG. 5 is a schematic illustration of an exemplary embodiment of a near-infrared spectroscopy sensor.

Referring now to FIG. 5, at least a physiological sensor 144 may include an optical sensor, which detects light emitted, reflected, or passing through human tissue. An "optical sensor," as used in this disclosure, is a device that uses various forms of light-matter (i.e., photon-atom) interactions to detect, interrogate, and quantify molecules. Optical sensor may include a near-infrared spectroscopy sensor (NIRS). A NIRS, as used herein, is a sensor that detects signals in the near-infrared electromagnetic spectrum region, having wavelengths between 780 nanometers and 2,500 nanometers. FIG. 5 illustrates an exemplary embodiment of a NIRS 500 against an exterior body surface, which may include skin. NIRS 500 may include a light source 504, which may include one or more light-emitting diodes (LEDs) or similar element. Light source 504 may, as a non-limiting example, convert electric energy into near-infrared electromagnetic signals. Light source 504 may include one or more lasers. NIRS 500 may include one or more detectors 508 configured to detect light in the near-infrared spectrum. Although the wavelengths described herein are infrared and near-infrared, light source 504 may alternatively or additionally emit light in one or more other wavelengths, including without limitation blue, green, ultraviolet, or other light, which may be used to sense additional physiological parameters 117. In an embodiment, light source may include one or more multi-wavelength light emitters, such as one or more multi-wavelength LEDs, permitting detection of blood-gas toxicology. Additional gases or other blood parameters so detected may include, without limitation $CO_2$ saturation levels, state of hemoglobin as opposed to blood oxygen saturation generally. One or more detectors 508 may include, without limitation, charge-coupled devices (CCDs) biased for photon detection, indium gallium arsenide (InGaAs) photodetectors, lead sulfide (PbS) photodetectors, or the like. NIRS 500 may further include one or more intermediary optical elements (not shown), which may include dispersive elements such as prisms or diffraction gratings, or the like. In an embodiment, NTRS 500 may be used to detect one or more circulatory parameters, which may include any detectable parameter further comprises at least a circulatory parameter. A sensor may include at least two sensors mounted on opposite sides of user's cranium.

Figure 6:
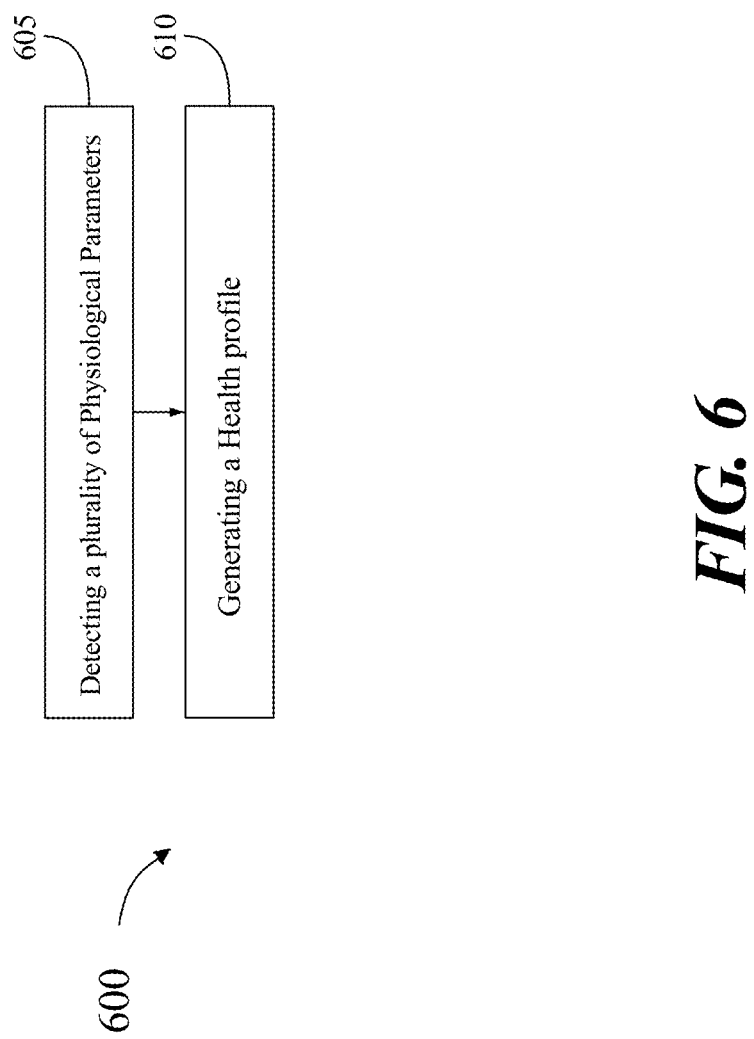
FIG. 6 is a flow diagram illustrating an exemplary method for generating a health profile for a user.

Referring now to FIG. 6, an exemplary method of generating a health profile of user. At step 605. Method includes detecting a plurality of physiological parameter utilizing at least a physiological parameter sensor helmet, as described and with reference to FIGS. 1-5. The physiological parameter sensor helmet includes at least a helmet further comprising a bone conduction transducer; and at least a sensor installed within the at least a helmet, wherein the at least a sensor is configured to measure plurality of physiological parameters of a user's, including at least a plurality of oxygenation signals. In some embodiments, the physiological sensor may include a near-infrared spectroscopy sensor configured to measure cranial blood-oxygenation signals from the user. The near-infrared spectroscopy sensor may include at least one optical sensor and at least one infrared light emitting diode. In some embodiments, the physiological sensor may include an oxygen hose of a mobile respiratory assembly. In some embodiments, the physiological sensor may include a skin temperature sensor configured to detect at least a skin temperature parameter as a function of at least a skin temperature. In some embodiments, the physiological parameter sensor helmet may include at least an environmental temperature sensor configured to detect an environmental temperature parameter as a function of an environmental temperature.

Still referring to FIG. 6, at step 610, method 600 includes generating a health profile utilizing a processor, as described and with reference to FIGS. 1-5. Generating the health profile includes receiving, by a processor, the plurality of physiological parameters from the at least a sensor; and generating, by the processor, the health profile as a function of plurality of physiological parameters. In some embodiments, the health profile may include a physiological alarm condition. Generating the health profile may include using a classification machine learning model. In some embodiments, method 600 may further include communicating, utilizing the processor, to at least a user interface an alert to a user as a function of the health profile. Method 600 may include generating an alert parameter as a function of the at least a physiological alarm condition in the health profile, wherein the at least a user interface is further configured to communicate the alert as a function of the alert parameter.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
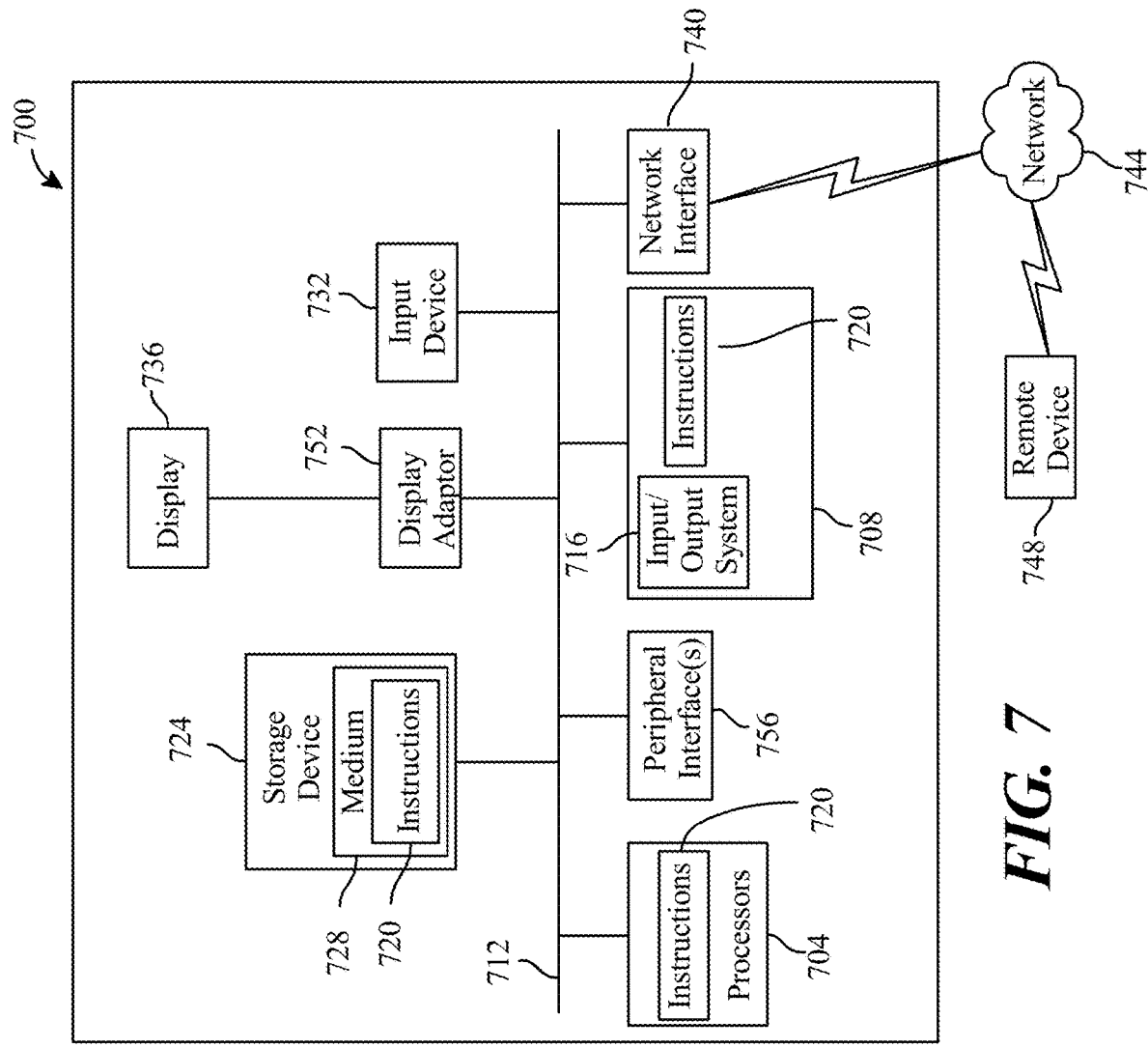
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A physiological parameter sensor helmet, the physiological parameter sensor helmet comprising:
    at least a helmet comprising a bone conducting transducer;
    at least a physiological sensor comprising at least one of an inhalation sensor and an exhalation sensor installed within the at least a helmet, wherein the at least a physiological sensor is configured to measure a plurality of physiological parameters of a user, wherein the plurality of physiological parameters comprises at least a plurality of blood oxygenation signals;
    a respiratory assembly configured to deliver a gas to the user as a function of the plurality of physiological parameters;
    a speaker configured to generate a noise-reducing sound; and
    a computing device in communication with the at least a physiological sensor and the speaker comprising:
        at least a processor; and
        a memory communicatively connected to the at least a processor, the memory containing instructions configuring the at least a processor to:
            receive an environmental noise signal;
            generate a noise-reducing sound signal as a function of the environmental noise signal;
            introduce the noise-reducing sound to the speaker as a function of the noise-reducing sound signal;
            receive the plurality of physiological parameters from the at least a physiological sensor; and
            generate a health profile as a function of the plurality of physiological parameters.
2. The physiological parameter sensor helmet of claim 1, wherein the at least a physiological sensor comprises a near-infrared spectroscopy sensor configured to measure a cranial blood-oxygenation signal from the user.
3. The physiological parameter sensor helmet of claim 2, wherein the near-infrared spectroscopy sensor comprises:
    at least one optical sensor and; and
    at least one infrared light emitting diode.
4. The physiological parameter helmet of claim 1, wherein:
    the respiratory assembly comprises a mobile respiratory assembly; and
    the at least a physiological sensor comprises an oxygen hose of the mobile respiratory assembly.
5. The physiological parameter sensor helmet of claim 1, wherein the at least a physiological sensor comprises a skin temperature sensor configured to detect at least a skin temperature parameter as a function of at least a skin temperature.
6. The physiological parameter sensor helmet of claim 1, further comprising:
    at least an environmental temperature sensor configured to detect an environmental temperature parameter as a function of an environmental temperature.
7. The physiological parameter sensor helmet of claim 1, wherein the health profile comprises a physiological alarm condition.
8. The physiological parameter sensor helmet of claim 1, further comprising:
    at least a user interface in communication with the at least a processor and configured to communicate an alert to the user as a function of the health profile.
9. The physiological parameter sensor helmet of claim 8, wherein:
    the memory contains instructions further configuring the at least a processor to generate an alert parameter as a function of at least a physiological alarm condition in the health profile; and
    the at least a user interface is further configured to communicate the alert to the user as a function of the alert parameter.
10. The physiological parameter sensor helmet of claim 1, wherein generating the health profile further comprises generating the health profile using a classification machine learning model.
11. A method for generating a health profile of a user, the method comprising:
    receiving, by at least a processor, an environmental noise signal;
    generating, by the at least a processor, a noise-reducing sound signal as a function of the environmental noise signal;
    generating, by a speaker, the noise-reducing sound as a function of the noise-reducing sound signal;
    detecting a plurality of physiological parameters utilizing a physiological parameter sensor helmet, the physiological parameter sensor helmet comprising:
        at least a helmet comprising a bone conducting transducer; and
        at least a physiological sensor comprising at least one of an inhalation sensor and an exhalation sensor installed within the at least a helmet, wherein the at least a physiological sensor is configured to measure the plurality of physiological parameters of a user, including at least a plurality of oxygenation signals;
    generating a health profile utilizing the at least a processor of a computing device,
        wherein generating the health profile comprises:

receiving, by the at least a processor, the plurality of physiological parameters from the at least a physiological sensor; and generating, by the at least a processor, the health profile as a function of the plurality of physiological parameters; and delivering a gas to the user utilizing a respiratory assembly as a function of the plurality of physiological parameters.

12. The method of claim 11, wherein the at least a physiological sensor comprises a near-infrared spectroscopy sensor configured to measure a cranial blood-oxygenation signal from the user.

13. The method of claim 12, wherein the near-infrared spectroscopy sensor comprises:
at least one optical sensor; and
at least one infrared light emitting diode.

14. The method of claim 11, wherein:
the respiratory assembly comprises a mobile respiratory assembly; and
the at least a physiological sensor comprises an oxygen hose of the mobile respiratory assembly.

15. The method of claim 11, wherein the physiological sensor parameter helmet further comprises a skin temperature sensor configured to detect at least a skin temperature parameter as a function of at least a skin temperature.

16. The method of claim 11, wherein the physiological parameter sensor helmet further comprises at least an environmental temperature sensor configured to detect an environmental temperature parameter as a function of an environmental temperature.

17. The method of claim 11, wherein the health profile comprises a physiological alarm condition.

18. The method of claim 11, further comprising:
communicating, utilizing at least a user interface in communication with the at least a processor, an alert to the user as a function of the health profile.

19. The method of claim 18, wherein generating the health profile further comprises:
generating, utilizing the at least a processor, an alert parameter as a function of at least a physiological alarm condition in the health profile; and
communicating, by the at least a user interface, the alert to the user as a function of the alert parameter.

20. The method of claim 11, further comprising:
generating, utilizing the at least a processor, the health profile using a classification machine learning model.

* * * * *